US00PP09253P

United States Patent [19]

Meilland

[11] Patent Number: Plant 9,253

[45] Date of Patent: Aug. 22, 1995

[54] HYBRID TEA ROSE PLANT NAMED 'MEISOYRIS'

[75] Inventor: Alain A. Meilland, Antibes, France

[73] Assignee: The Conard-Pyle Company, West Grove, Pa.

[21] Appl. No.: 283,801

[22] Filed: Jul. 25, 1994

[51] Int. Cl.[6] ..... A01H 5/00
[52] U.S. Cl. ..... Plt./20
[58] Field of Search ..... Plt. 20, 21

[56] References Cited

U.S. PATENT DOCUMENTS

P.P. 5,608 12/1985 Winchel ..... Plt./20

*Primary Examiner*—Howard J. Locker
*Attorney, Agent, or Firm*—Burns, Doane, Swecker & Mathis

[57] ABSTRACT

A new and distinct variety of Hybrid Tea rose plant is provided which abundantly and continuously forms large attractive fragrant blossoms that are Strawberry Red on the upper surface and Cardinal Red on the under surface. Such blossoms are long lasting and exhibit good petal-drop characteristics. The plant exhibits a semi-erect growth habit, rather vigorous vegetation, forms bright decorative foliage, and is well suited for use as attractive ornamentation in the landscape. Additionally, the plant exhibits good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Nuage Parfumé variety (U.S. Plant Pat. No. 2,574). The Nuage Parfumé variety sometimes is known as the Duftwolke variety or the Fragrant Cloud variety. The male parent (i.e, the pollen parent) was formed by the cross of the Oklahoma variety (U.S. Plant Pat. No. 2,326) and the Duftzauber 84 variety (nonpatented in the United States). The parentage of the new variety can be summarized as follows:

Nuage Parfumé × (Oklahoma × Duftzauber 84).

The seeds resulting from the above pollination were sown and 38 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis large attractive fragrant long-lasting blossoms that are Strawberry Red on the upper surface and Cardinal Red on the under surface,
(b) exhibits a semi-erect growth habit with bright decorative foliage,
(c) exhibits rather vigorous vegetation,
(d) is particularly suited for growing in the landscape, and
(e) exhibits good disease resistance.

The new variety well meets the needs of the horticultural industry and is particularly well suited for use as attractive ornamentation in the landscape. A regular-appearing plant is produced wherein highly attractive red blossoms contrast nicely with the bright decorative foliage.

The new variety has been found to undergo asexual propagation in France by a number of routes, including budding, grafting, cuttage, etc. The characteristics of the new variety have been found to be stable and are strictly transmissible by such asexual propagation from one generation to another.

The new variety has been named to the Meisoyris variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during September while budded on *Rosa froebelii* understock and growing outdoors at Le Cannet des Maures, Var, France.

DETAILED DESCRIPTION

Figures 1, 2, 3, 4, 5, 6, 7, 8, 9, 10, 11, 12, 13, 14, 15, 16:
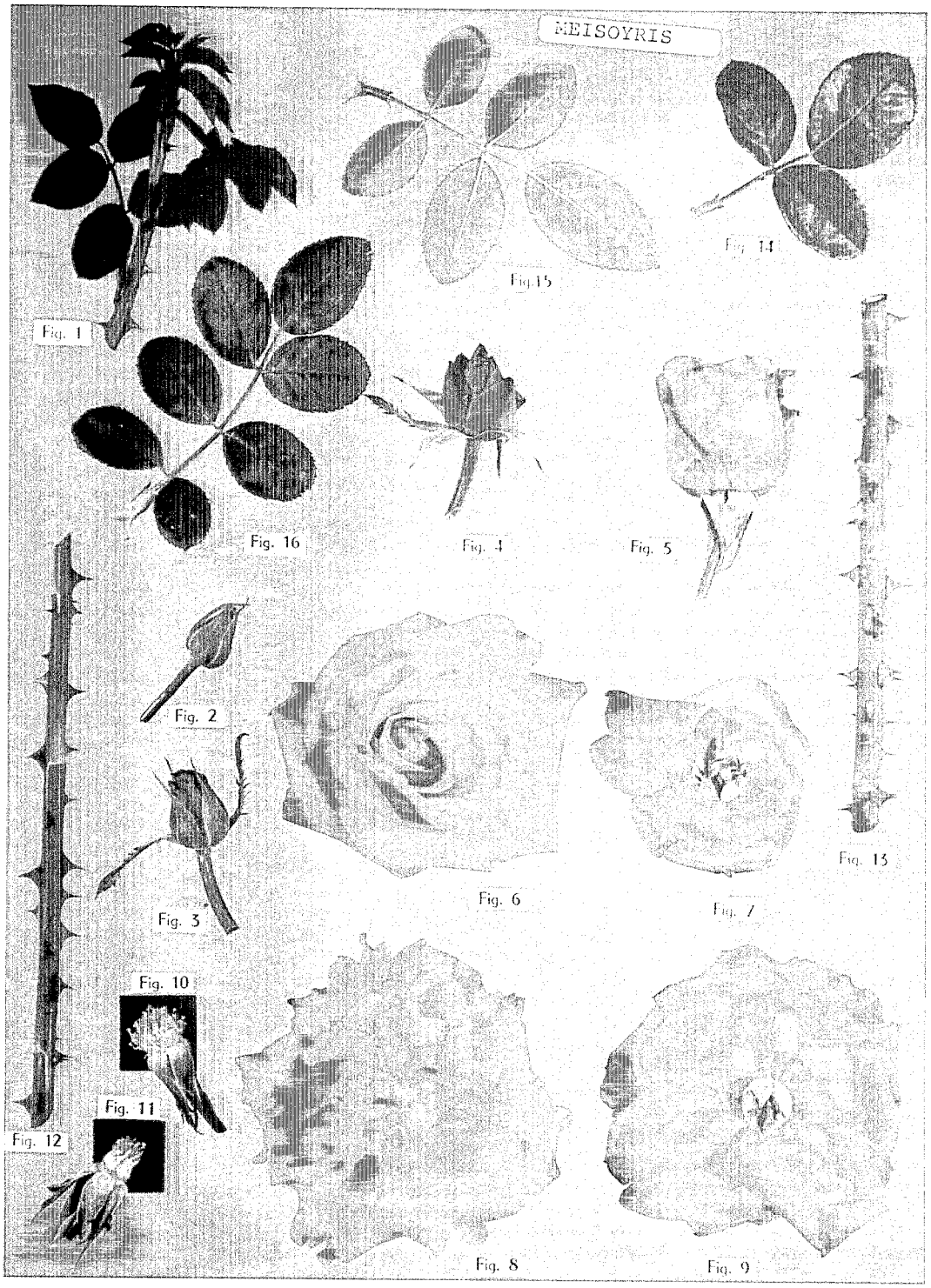
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates specimens of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of three year-old plants during September while budded on *Rosa froebelii* understock and growing outdoors at Le Cannet des Maures, Var, France. The coloration in common terms precedes reference to the chart.

Class: Hybrid Tea.

Plant:

*Height.*—Approximately 70 to 80 cm. on average at the end of the growing season.

*Habit.*—Semi-erect.

Branches:

*Color.*—Young stems: reddish in coloration. Adult wood: medium green, Yellow-Green Group 146B.

*Thorns.*—Size: medium. Quantity: moderately numerous. Color: reddish on young stems and pinkish on mature wood.

Leaves:

*Stipules.*—Adnate, pectinate, rather wide, and linear.

*Petioles.*—Upper surface: reddish brown on young foliage and medium green on adult foliage with more or less glandular edges. Under surface: medium green with a few prickles.

*Leaflets.*—Number: 3, 5 (most often), and 7. Shape: oval. Serration: single and regular. Texture: leathery. General appearance: rather dense and semi-glossy. Color (young foliage): Upper surface: medium green, Green Group 137A, and widely suffused with reddish coloration. Under surface: light green, Green Group 137C, and widely suffused with reddish coloration. Color (adult foliage): Upper surface: dark green, Green Group 139A. Under surface: light green, Green Group 137C.

Inflorescence:

*Number of flowers.*—Generally borne singly, but sometimes occur in clusters of 2 to 4.

*Peduncle.*—Medium green, and more or less toned with reddish coloration. The length is approximately 4 cm on average.

*Sepals.*—Upper surface: tomentose, greenish in coloration and commonly possess appendiculated edges. Under surface: light green with more or less glandular and slightly appendiculated edges.

*Buds.*—Shape: conical. Length: approximately 3.5 cm. on average. Size: large. Color upon opening: Upper surface: Ruby Red, Red-Purple Group 59A. Under surface: Ruby Red, Red-Purple Group 59A.

*Flower.*—Shape: cuplike and double. Diameter: approximately 13 to 14 cm. on average. Color (when opening begins): Upper surface: Currant Red, Red Group 46A. Under surface: Currant Red, Red Group 46A. Color (when blooming): Upper surface: Strawberry Red, Red Group 46B. Under surface: Cardinal Red, Red Group 53C. Color (at end of opening): Upper surface: Strawberry Red, Red Group 46B. Under surface: Cardinal Red, Red Group 53C. Fragrance: strong. Lasting quality: very long. During the spring and late fall the blossoms commonly last 8 to 9 days when cut and placed in a vase and approximately 11 to 12 days on the plant. During mid-summer the blossoms commonly last approximately 6 days when cut and placed in a vase and approximately 8 to 9 days on the plant. Petal shape: oval with cuneate shape at base. Petal drop: good. Stamen number: approximately 95 on average. Anthers: normal golden yellow in coloration. Filaments: dark fuchsia in coloration, and commonly of irregular heights. Pistils: approximately 68 on average. Stigmas: normal. Styles: tomentose near the base, fuchsine and commonly of irregular heights. Receptacle: medium green, smooth, and in longitudinal section in the shape of a large funnel.

Development:

*Vegetation.*—Rather vigorous.

*Blooming.*—Very abundant and continuous.

*Aptitude to bear fruits.*—Normal.

*Resistance to frost.*—Good.

*Resistance to diseases.*—Very good. The resistance to powdery mildew is generally comparable to that of the best previously available varieties of the class. The resistance to black spot is a little better than that of the Double Delight variety (U.S. Plant Pat. No. 3,847).

I claim:

1. A new and distinct variety of Hybrid Tea rose plant characterized by the following combination of characteristics:

(a) forms in abundance on a continuous basis large attractive fragrant blossoms that are Strawberry Red on the upper surface and Cardinal Red on the under surface, (b) exhibits a semi-erect growth habit with bright decorative foliage, (c) exhibits rather vigorous vegetation, (d) is particularly suited for growing in the landscape, and (e) exhibits good disease resistance;

substantially as herein shown and described.

* * * * *

MEISOYRIS